United States Patent [19]

Black

[11] 4,018,919
[45] Apr. 19, 1977

[54] SEQUENTIAL CONTRACEPTIVE METHOD USING TWO TYPES OF PROGESTATIONAL AGENTS

[75] Inventor: Larry J. Black, Indianapolis, Ind.

[73] Assignee: Eli Lilly and Company, Indianapolis, Ind.

[22] Filed: July 16, 1975

[21] Appl. No.: 596,542

[52] U.S. Cl. .................................. 424/242; 424/243
[51] Int. Cl.² ......................................... A61K 31/565
[58] Field of Search ............................ 424/242, 243

[56] References Cited

UNITED STATES PATENTS

| | | | |
|---|---|---|---|
| 3,366,651 | 1/1968 | Lefebvre | 424/242 X |
| 3,409,721 | 11/1968 | Applezweig | 424/242 X |
| 3,499,013 | 3/1970 | Benn | 424/242 X |
| 3,711,521 | 1/1973 | Coombs et al. | 424/243 X |
| 3,758,687 | 9/1973 | Ufer et al. | 424/243 |
| 3,795,734 | 3/1974 | Rochefort | 424/242 X |
| 3,892,842 | 7/1975 | Zaffaroni | 424/242 X |

*Primary Examiner*—Albert T. Meyers
*Assistant Examiner*—Vera C. Clarke
*Attorney, Agent, or Firm*—James L. Rowe; Charles W. Ashbrook; Everet F. Smith

[57] ABSTRACT

Sequential administration of specified progestational agents to a female mammal during the follicular and luteal phases of the sexual cycle provides a novel and effective method of contraception.

7 Claims, No Drawings

SEQUENTIAL CONTRACEPTIVE METHOD USING TWO TYPES OF PROGESTATIONAL AGENTS

BACKGROUND OF THE INVENTION

The commonly used method of oral contraception in human females consists of a combination of estrogen and progestin (progestational agent) administered daily for 21 days. Menstruation occurs about 3 to 5 days after withdrawal and administration is reinitiated after 8 days, thereby beginning a new cycle. Inhibition of ovulation is believed to be the primary mechanism of this contraceptive method. Rudel, et al., *Fertility and Sterility*, 16, 158–169 (1965) pointed out, however, that progestins, in addition to their antiovulatory action, have other antifertility effects including the production of a state of maturation of the endometrium which is out of phase with ovulation, accompanied by changes in the cervical mucus, these changes being incompatible with vital and motile spermatozoa. The authors suggested that, in an oral contraceptive agent comprising a combination of progestin and estrogen, these other effects (in addition to inhibiting ovulation) of progestins may be lost in the presence of estrogen. Martinez-Manaoutou, et al., ibid, 17, 49–57 (1966) has also suggested that a low dose of a progestin, specifically chlormadinone acetate, would prevent conception when administered continuously at the rate of 0.5 mg. per day to human females during the entire ovulatory cycle. It was determined that ovulation probably occurred in 60 percent of the patients. Only one pregnancy occurred in 416 patients and 1600 menstrual cycles. From these observations, the authors advocated the continuous administration of minimal doses of a progestin as a contraceptive method in human females. The same laboratory reported, ibid, 17, 57–62 (1967) that chlormadinone acetate, when administered to human females at a dosage of less than 500 mcg. daily, demonstrated antiestrogenic influence on the cervical mucus without suppression of endometrial development. The contraceptive effectiveness of the administered progestational agent appeared to parallel closely the changes in the cervical mucus. The same research group ibid, 18, 219–221 (1967) repeated their previous findings that a progestin, given at dose levels which do not inhibit ovulation, is able to create a state of hormonal inbalance as evidenced by a suppressed endometrium and/or a thickened, scanty cervical mucus. The daily low level administration of a progestin throughout the menstrual cycle was the contraceptive method advocated by the authors for human population control on a large scale. For this purpose, they specifically advocated the employment of an implanted pellet which would meter out the progestin for a month or six weeks.

In summary, the research group headed by Martinez-Manaoutou has found that the low daily dosage of chlormadinone acetate (0.5 mg. daily) throughout the menstrual cycle affords an effective contraceptive method.

U.S. Pat. No. 3,758,687, issued Sept. 11, 1973, discloses the administration to a female human at some point during the interval from the 5th to the 8th day of the menstrual cycle of an amount of a progestin sufficient to prevent conception during the remainder of the cycle. The patented process contemplates the administration of a single dose sufficient to last an entire cycle as an improvement over administration of daily low doses.

A relationship between the progestational state of the uterus and implantation was reported originally by Corner and Allen, *Am. J. Physiol.*, 86, 74 (1928), 88, 340 (1929). The necessity of pretreatment with the follicular hormone (estrogen) for optimal response to the luteal hormone (progesterone) was later observed by many others including Allen, *Am. J. Physiol.*, 92, 612 (1930) and Hisaw and Leonard, *Am. J. Physiol.*, 92, 574 (1930). The phenomenon of sequential influence of ovarian steriods is now widely accepted by research workers studying mammalian reproductive cycles and two phases (follicular and luteal) are recognized.

Estrogen priming is, however, apparently not indispensable for a progestational response, but priming lowers the threshold for uterine responses, including progestational proliferation, increased carbonic anhydrase, [Pincus et al. *Endocr.*, 61, 528 (1957)], and synthesis of DNA and mitosis, [Lee and Dukelow, *J. Reprod. Fert.*, 31 473 (1972)]. Rudel, et al., *J. Reprod. Fert.*, 8, 305 (1964), observed that the progestational response to chlormadinone acetate, a typical progestin, in humans is directly related to the degree of estrogen stimulation of the endometrium at the time treatment is started.

Black, *Fertil. Steril.*, 25, 575 (1974), found that administration of progestins in the proliferative phase of the menstrual cycle altered the progestational state of the endometrium in the luteal phase of the cycle, but continuous treatment nullified the effect. Black suggested that a novel contraceptive method might involve the administration of a progestin, preferably at low dosage levels, to the female mammal only during the proliferative phase of the cycle.

Moghissi et al., writing in *Obstetrics and Gynecology*, 41, 585 (1973), discussed the mechanism whereby a micro dose of a progestin, norethindrone, administered daily for 30 days prevented conception. The authors found that at least three different factors were involved: alternation of ovulation and progesterone production by the corpus luteum, cervical mucus changes and inhibition of sperm transport, and endometrium changes.

McDonald and coworkers, writing in *J. Obstet, Gynaec. Brit. Cwlth.*, 75, 1123 (1968), discuss results obtained with a progestin tablet in which the progestin is chlormadinone acetate, the progestin acting as an oral contraceptive. The amount of chlormadinone acetate used was 0.5 mg. (500mcg.) daily. It was the authors' opinion that the continous low dose administration of a progestin throughout the menstrual cycle had advantages over the usual oral contraceptive dosage regimen.

Nygren et al., writing in *Contraception*, 9, 249 (1974), disclosed the contraceptive efficacy of 10 and 25 mgs. norethindrone administered post-ovulatory to human females.

Sakiz, et al. *Hormonal Steroids*, Proceedings of the Third International Congress, Hambrug, September, 1970 (Excerpta Medica International Congress Series No. 219), pages 865–871, compared the hormonal properties of a new compound, R2323 (13-ethyl-17α-ethynyl-17β-hydroxy-gona-4,9,11-trien-3-one) with norgestrienone, its 13-methyl homolog, with norethindrone (17α-ethynyl-19-nortestosterone) and with norgestrel, the 13-ethyl homolog of norethindrone. A further study of the antifertility effects of this new compound is provided by Sakiz et al., *Contraception*, 10, 467 (1974).

Four contraceptive regimens have recently been patented. Kincl, U.S. Pat. No. 3,822,355, advocates employing a regimen in which a placebo is administered to the female beginning with the first day of menstruation for 16 days and then following ovulation, a progestional agent is administered for the next four days. The dosage is said to be sufficient to inhibit the function of the corpus luteum. The remaining days of the cycle, the patient receives from 10 to 40 percent of the previous progastational agent dosage. Rudel and Kincl, U.S. Pat. No. 3,836,651, advocate administering to a female starting on the fifth day of the menstrual cycle and continuing for 20 to 21 days thereafter a single daily dose of an estrogen and a progestational agent, the estrogen dosage being extremely low. Rochefort, U.S. Pat. No. 3,795,734, advocates a regimen in which consecutive daily doses of a progestin are given during the early phase of the cycle followed by consecutive daily dose of an estrogen-progestin combination during mid-cycle and in the final phase of the cycle a progestin only.

Presently approved oral contraceptive regimens which have been employed either in the United States or overseas include the most widely used procedure involving the use of a combination of progestin and estrogen during 20–21 days of a sexual cycle. This regimen has been implicated in production of an increased incidence of thrombosis. A "minipill" regimen has been tried in which the quantities of progestin and estrogen are greatly reduced from those originally employed, but the same hormones are administered during the menstrual cycle. A second "minipill" regimen involves the use of the progestin only in very small daily doses. This latter regimen may avoid the thrombosis problem associated with estrogen administration but suffers from other side effects particularly including irregular bleeding and also from lowered efficacy. Most of the current research effort in this area is devoted to finding contraceptive regimens using much lower hormonal doses and avoiding administration of an estrogen entirely.

Edgren et al., writing in *Fertility and Sterility*, 18, 238 (1967), categorized progestational agents in five classes. Several biological tests for determining the properties of each progestational agent with a view to classifying the agent are set forth in this article. Black and Kraay, *J. Steroid Biochem.*, 4, 467 (1973), divide progestational agents into two classes, A and B, depending upon their ability to interact with uterine cytoplasmic receptor sites for estrogen. Their test is based upon the ability of a progestational agent to act as an anti-estrogenic substance by its direct effect on the binding of tritiated estradiol with uterine cytoplasmic receptors, and it was observed by the authors that tritiated estradiol uptake was inhibited by compounds which interacted with the receptors (type A). Type B progestational agents, on the other hand, did not interact with these uterine cytoplasmic receptor sites and, apparently, derived their antiestrogenic effects (characteristic of all progestins) by a different process.

It is an object of this invention to provide an oral contraceptive method which avoids the adverse effects associated with currently employed or suggested contraceptive procedures but which also provides a satisfactorily low pregnancy rate.

SUMMARY OF THE INVENTION

In fulfillment of the above and other objects, this invention provides an oral contraceptive regimen comprising the two phase administration of progestational agents to a female mammal during a sexual cycle. Specifically, according to my novel contraceptive method, a Type B progestational agent as defined by Black and Kraay (loc. cit.) is administered to the cycling female mammal on the day following the cessation of bleeding in primates, continuing during the first half or follicular or proliferative phase of the cycle. During the second half or the luteal or secretory phase of the cycle, another specific type of progestational agent or progestin, a Type A agent as defined by Black and Kraay, is administered. With an average human female, for example, this method of contraception involves self-administration by the cycling female of a Type B progestational agent for the period beginning on day 6 and continuing through day 16 of the cycle. Self-administration of a Type A progestational agent would then begin on day 17 and continue through day 28. A preferred Type B progestin useful prior to ovulation in the contraceptive process of this invention is chlormadinone acetate (6-chloro-6-dehydro-17α-acetoxy-progesterone.) A preferred Type A progestin to be applied in the luteal phase is norethindrone (17α-ethynyl- 17β-hydroxy-estra-4-en-3-on). During the follicular phase of the menstrual cycle, a dose or amount of a Type B progestin equivalent to 0.166 to 8.33 mcg. of chlormadinone acetate per day per kg. of female mammalian body weight is administered. During the luteal phase of the menstrual cycle, a dose or amount of a Type A progestin equivalent of 0.0017 to 0.0833 mg. of norethindrone per day per kg. of female mammalian body weight is administered. For an average 60 kg. human female, the daily dose amount of a preovulation Type B progestin would be equivalent to from 10 to 500 mcg. of chlormadinone acetate and the dose amount of Type A progestin equivalent to 0.1 to 5 mg. norethindrone per day.

In general, Type B steriods useful in the contraceptive process of this invention in the follicular phase can be considered to be derivatives of progesterone, the naturally occurring hormone. Progesterone has the basic perhydro cyclopentanophenanthrene structure with 19 carbons dispersed in four rings with a two-carbon side chain in the β-orientation at $C_{19}$. Among such steroids are progesterone (pregn-4-ene-3,20-dione), norprogesterone (17β-acetyl-estra-4-en-3-one), provera (17-hydroxy-6α-chloropregn-4-ene-3,20-dione acetate), 16α-chloro-progesterone (16α-chloropregn-4-ene-3,20-dione), 6α-chloro-16α-methylprogesterone (6α-chloro-16α-methyl-pregn-4-ene-3,20-dione), $\Delta^{4,9}$-progesterone [19-nor-4,9-(10)-pregnadiene-3,20-dione], and the like. In addition, norgestrel (dl -13β-ethyl-17α-ethynyl-17β-hydroxy-gon-4-en-3-one), which cannot be classed as a progesterone derivative, is a Type B progestin by the Black-Kraay test procedure. The second class of progestin to be used in the luteal phase — Type A progestins by the Black-Kraay criteria — in general resemble estrone in that they lack an angular methyl group between the A and B rings. They differ from estrone, however, in that the A ring is no longer aromatic but has been hydrogenated. Typical Type A progestins include: norethindrone (17α-ethynyl-17β-hydroyestr-4-en-3-one), norethynodrel (17α- ethynyl-estr-5(10)-en-3β,17-diol), norethandrone (17α-ethyl-19-nortestosterone), and the like.

Any given progestin will be classified by the Black-Kraay definition as to whether it is Type B — useful in the preovulation phase of the cycle, or Type A — useful in the postovulatory phase. Type B progestins by the Black-Kraay definition correspond to classes 1 and 2 of Edgren et al., (loc. cit. page 252), and Type A progestins to class 3.

As set forth above, the dosage levels of progestational agents useful for administration in the follicular or luteal phases of the sexual cycle respectively are based upon doses equivalent to the useful dose of either chlormadinone acetate or of norethindrone. Dosages of these other progestational agents which are equivalent to the above range of doses set forth for chlormadinone acetate or for norethindrone depend upon both the nature of the compound and the route of administration. For example, norethandrolone is five times more active than progesterone subcutaneously but 50 times more active orally. Chlormadinone acetate is 50 times more active than norethandrolone and 500 times more active than norethindrone by injection and 50 times more active than either orally. Equivalencies of other progestational agents to chlormadinone acetate or to norethindrone can be determined experimentally, and their dosage levels in my novel process can in turn be determined from these data.

The anti-fertility effect of the administration of a Type B progestin during the follicular phase of the cycle followed by the administration of a Type A progestin during the luteal phase of the cycle is illustrated by the following experminent:

Mature Dutch Belted rabbits weighing 2 to 3 kg. were used. The rabbits were housed individually under controlled lighting consisting of 14 hours light (6:00 a.m. to 8:00 p.m.) and 10 hours darkness. Females were isolated for at least 3 weeks prior to use.

All injections were given subcutaneously once daily in 0.5 ml. corn oil vehicle. The day of mating or artificial insemintion was considered day 0 and all animals were sacrificed on day 10 of pregnancy. At that time the ovaries were examined for evidence of ovulation and animals without such evidence were disregarded. The number of ovulations and embryos were then recorded.

Postovulatory activity was determined by mating females with males of proven fertility. Vagnial smears were taken to establish the presence of motile sperm. The animals were then injected from day 0 to 9.

Pregnancy was induced by artificial insemination and intravenous injection of 100 I.U. HCG for evaluation of preovulatory, continuous and sequential treatment. Ejaculates were collected with an artificial vagina from males of established fertility. Individual ejaculates were diluted to a total volume of 1.25 ml. with sterile saline and 0.25 ml. was inseminated into four females. Control animals were inseminated with every ejaculate used.

Preovulatory treatment consisted of daily injection for the 5 days preceding insemination, and this treatment was extended through day 9 for the continuous regimen. Sequential treatment was composed of a Type B progestin preovulatory and a Type A progestin postovulatory treatment within the same animals.

For statistical evaluation of the data the response variable analyzed was the proportion of embryos to ovulations. Pregnancy was induced by two methods and a t-test of the control groups indicated a significant difference. Thus, comparisons were made between groups subjected to similar pregnancy induction technique. Analysis of variance revealed that comparisons among treatments had to be made at specific dose levels rather than among averaged treatment methods. Duncan's Multiple Range Test [Biometrics, 11, 1–42 (1955) — see also Wilcoxson and Wilcox, *Some Rapid Approximate Statistical Procedures*, Lederle Laboratories, Pearl River, New York 1964 — page 7] was used to determine the difference of each treatment from the appropriate control and also to determine differences between treatments at the 0.10 level of significance.

A series of experiments were carried out according to the above general procedure to determine the differences between preovulatory and continous administration of Type A and B progestins; norethindrone and chlormadinone acetate respectfully. Table I gives the results of these determinations. In the Table, column 1 gives the treatment; column 2, the daily dose in mgs.; column 3, the number of pregnancies; column 4 the average proportion (ratio) of embryos to ovulations; and column 5 the activity (o or +) and statistical significance.

Table I

THE INFLUENCE OF PREOVULATORY OR CONTINUOUS ADMINISTRATION OF CHLORMADINONE ACETATE OR NORETHINDRONE ON FERTILITY IN THE RABBIT

| Treatment | Dose/Day (mg) | Pregnancies | Average Proportion Embryos Ovuluations | Activity * | ** |
|---|---|---|---|---|---|
| Control | | 38/41 | .686 | | a |
| Preovulatory | | | | | |
| Chlormadinone acetate | .003 | 4/4 | .581 | 0 | a |
| " | .01 | 2/6 | .210 | + | b |
| " | .03 | 0/3 | 0.0 | + | b |
| " | .10 | 0/6 | 0.0 | + | b |
| " | .20 | 0/5 | 0.0 | + | b |
| Norethindrone | .10 | 2/2 | .678 | 0 | a |
| " | .50 | 1/5 | .060 | + | b |
| " | 5.0 | 0/3 | 0.0 | + | b |
| Continuous | | | | | |
| Chlormadinone acetate | .01 | 6/9 | .512 | 0 | a |
| " | .03 | 0/3 | 0.0 | + | b |
| Norethindrone | .10 | 3/3 | .869 | 0 | a |
| " | .50 | 3/3 | 675 | 0 | a |
| " | 1.0 | 0/3 | 0.0 | + | b |

*++ = different from control; :0 = not different from control
**Any two average proportions with a common letter are not significantly different at the .10 level of significance using Duncan's Multiple Range Test.

According to Table I, both progestins were active, but a distinct advantage in potency was apparent with chlormadinone acetate. However, on the response curve of each compound there existed a dose where it was active by preovulatory treatment, and inactive by continuous administration. This situation occurred at 10 μg. with chlormadinone acetate and at 500 μg. with norethindrone.

Table II gives similar data on the effect of postovulatory administration of each progestin on pregnancy induced by natural mating.

Table II

THE INFLUENCE OF POSTOVULATORY ADMINISTRATION OF CHLORMADINONE ACETATE OR NORETHINDRONE ON FERTILITY IN THE RABBIT

| Treatment | Dose/Day (mg) | Pregnancies | Average Proportion Embryos Ovulations | Activity * | ** |
|---|---|---|---|---|---|
| Control |  | 26/26 | .851 |  | a |
| Chlormadinone acetate | .10 | 3/3 | .933 | 0 | a |
| " | .20 | 3/3 | .915 | 0 | a |
| " | 1.0 | 3/3 | .952 | 0 | a |
| " | 10.0 | 5/5 | .894 | 0 | a |
| Norethindrone | 1.0 | 3/3 | .944 | 0 | a |
| " | 5.0 | 0/4 | 0.0 | + | b |
| " | 10.0 | 0/4 | 0.0 | + | b |
| " | 10.0 | 0/2 | 0.0 | + | b |

*+ = different from control; 0 = not different from control
**Any two average proportions with a common letter are not significantly different at the .10 level of significance using Duncan's Multiple Range Test.

Postovulatory administration of a Type A and a Type B progestin established a distinct difference between the two types. Norethindrone, a Type A progestin inhibited fertility at 5 mg. and higher dose levels whereas chlormadinone, a Type B progestin, was inactive in this regard at dosages up to 10 mg.

Table III shows experimental results obtained when sequential progestin administration was employed comparing in each instance, Type B progestin administration in the follicular phase of the sexual cycle followed by a Type A progestin adminstration in the luteal phase, with a Type B progestin only in the follicular phase or a Type A progestin alone in the luteal phase.

Table III

THE INFLUENCE OF SEQUENTIAL ADMINISTRATION OF CHLORMADINONE ACETATE AND NORETHINDRONE ON FERTILITY IN THE RABBIT

| Treatment | Dose/Day (mg) | Pregnancies | Average Proportion embryos/ Ovulations | Activity * | ** |
|---|---|---|---|---|---|
| A | | | | | |
| Sequential Chlormadinone acetate (pre) | .003 | 2/6 | .197 | + | a |
| Norethindrone (post) | 1.10 | | | | |
| Chlormadinone acetate (pre) | .003 | 4/4 | .581 | 0 | b |
| Control (inseminated) |  | 38/41 | .686 |  | b |
| B | | | | | |
| Sequential Chlormadinone acetate (pre) | .003 | 2/6 | .197 |  | a |
| Norethindroneo (post) | 1.0 | | | | |
| Norethindrone (post) | 1.0 | 3/3 | .944 |  | b |

*+ = different from control; 0 = not different from control
**Any two average proportions with a common letter are not significantly different at the .10 level of significance using Duncan's Multiple Range Test.
***The comparison of Norethindrone to the combination was made using the Wilcoxon Rank Sum Test (23) on the adjusted proportions. The adjustment was made by subtracting the proper control average proportion from the observed proportion for each animal.

From the data in Table III, it can be seen that the combination of 3 mcg. (.003 mg.) of chlormadinone acetate administered during the follicular phase followed by 1 mg. of norethindrone administered during the luteal phase to the same group of rabbits decreased the number of pregnancies compared to administration of a compound only in a single phase of the cycle from 100 percent (4/4 and 3/3 to 4/11 with a decrease in the average proportion of embryos to ovulations from 0.581 and 0.944 respectively) to 0.197. The combination is thus more effective than the preovulatory (follicular) administration of 10 mcg. of chlormadinone acetate alone (Table I). By contrast it can be seen that administration of chlormadinone acetate postovulatory is without effect upon fertility (Table II) and that administration of 10 mcg. of chlormadinone acetate throughout the cycle (Table I) is less effective than the administration of 10 mcg. of chlormadinone acetate only during the preovulatory phase (Table II). Additionally, norethindrone is without effect on fertility when administered in the postovulatory phase at the dose of 1 mg. It should be emphasized, however, that the combined regimen of the minimal chlormadinone acetate dose followed by the minimal norethindrone dose, 3 mcg. and 1 mg. respectively, is a far more effective contraceptive method than the use of either compound by itself in its particular phase of the menstrual cycle and the activity of the sequential combination is comparable to the use of far higher doses of chlormadionone by itself in the follicular phase or by far higher doses of norethindrone by itself in the luteal phase. It is thus apparent that the contraceptive process of this invention makes possible the use of lower doses of the two types of progestational agents employed sequentially than is possible with either type of progestational agent used by itself in a single phase of the cycle.

Progestins useful in the novel contraceptive process of this invention are administered to female mammals either orally or parenterally. The active progestins, in general those compounds which possess a 17α-acetoxy or 17α-ethynyl group, are conveniently administered in the form of tablets or capsules. For administration in these pharmaceutical forms, the compound is mixed with a pharmaceutically-acceptable excipient and the mixture either loaded into telescoping gelatin capsules or binders; lubricants and the like are also added and the new mixture pressed into tablets. Each tablet or capsule contains a dose of the progestin sufficient to prevent conception when taken daily during the follicular phase. With those progestins which are not orally active, as for example progesterone itself, the compound is preferably administered intramuscularly or intraperitoneally to the female mammal. This parenteral mode of administration is preferred for those mammals who are unable to take oral medication. In carrying out the novel processes of this invention with human females, however, the oral mode of administration is preferred. For such purposes, the medication is placed in a dispenser containing a calendar on its face and 21 or 28 pill slots. On a 21-day regimen, the first 10 slots are filled with tablets containing a Type B progestin and the last 11 slots are filled with tablets containing a Type A progestin. With the 28-day dispenser, the first 10 slots are filled with the Type B progestin-containing tablets, the next 11 slots are filled with the Type A progestin-containing tablets, and the last seven slots are filled with placebo tablets. In either case, the human female takes pill number 1 on day 1 which is the first day after the cessation of bleeding from her last menstrual period and continues till the dispenser is empty starting with a new dispenser on day 1 of her next cycle. An alternative mode of adminstration would involve a dispenser with the first seven slots filled with placebo tablets, then 10 slots filled with the Type B progestin medication followed by 11 slots again filled with Type A progestin tablets. With this dispenser, the human female would take the first placebo tablet on the first day of menstruation.

I claim:

1. A method of contraception for female mammals which comprises the administration to a female mammal of a Type B progestin during the follicular phase of the sexual cycle and a Type A progestin during the luteal phase fo the sexual cycle, at dose levels sufficient to prevent conception.

2. The method according to claim 1 in which the Type B progestin is chlormadinone acetate and the Type A progestin is norethindrone.

3. The method according to claim 1 in which the Type B progestin is administered at a rate equivalent to administration of 0.166 to 8.33 mcg. of chlormadinone per kg. of female body weight per day and the Type A progestin is administered at a rate equivalent to administration of 0.0017 to 0.0833 mg. of norethindrone per kg. of female body weight per day.

4. A method of contraception for human females which comprises oral administration to a human female of a Type B progestin during the follicular phase of the menstrual cycle — from about day 6 through day 16 — and a Type A progestin during the luteal phase of the menstrual cycle — from about day 17 through day 28.

5. The method according to claim 4 in which chlormadinone is the Type B progestin and norethindrone is the Type A progestin.

6. The method according to claim 4 in which the daily dosage level of the Type B progestin in the follicular phase is equivalent to of 10–50 mcg. of chlormadinone and the daily dosage level of the Type A progestin in the luteal phase is equivalent to 0.1–5 mg. of norethindrone.

7. A contraceptive process which comprises oral administration to a human female of from 10–500 mcg. of chlormadinone daily during the follicular phase of the menstrual cycle — day 6 day 16 — followed by administration of 0.1 – 5 mg. of norethindrone daily during the luteal phase of the menstrual cycle.

* * * * *